US00PP16547P2

(12) United States Plant Patent
Parks

(10) Patent No.: US PP16,547 P2
(45) Date of Patent: May 16, 2006

(54) ***CAMELLIA* PLANT NAMED 'CLASSIC PINK'**

(50) Latin Name: *Camellia japonica*
Varietal Denomination: Classic Pink

(76) Inventor: Clifford Robert Parks, 125 Carolina Forest Rd., Chapel Hill, NC (US) 27516

( * ) Notice: Subject to any disclaimer, the term of this patent is extended or adjusted under 35 U.S.C. 154(b) by 108 days.

(21) Appl. No.: 10/811,043

(22) Filed: Mar. 27, 2004

(51) Int. Cl.
*A01H 5/00* (2006.01)

(52) U.S. Cl. ..... Plt./244

(58) Field of Classification Search ..... Plt./244
See application file for complete search history.

*Primary Examiner*—Kent Bell

(57) ABSTRACT

A new cultivar of *Camellia* named 'Classic Pink' that is characterized by exceptional cold-hardiness, an attractive compact plant form with very dark glossy green foliage, and formal double very pale pink flowers which are late to bloom. In combination these traits set 'Classic Pink' apart from all other existing varieties of *Camellia* known to the inventor.

2 Drawing Sheets

Genus: *Camellia.*
Species: *japonica.*
Denomination: 'Classic Pink'.

BACKGROUND OF THE INVENTION

The present invention relates to a new and distinct cultivar of *Camellia* that is grown as an ornamental evergreen flowering shrub. The new cultivar is known botanically as *Camellia japonica* and will be referred to hereinafter by the cultivar name 'Classic Pink'.

In 1962, the inventor commenced a *Camellia* breeding program whose primary objective was the development of varieties with significantly increased cold hardiness, thereby affording consumers in colder regions the opportunity to enjoy *Camellias.* In addition to breeding for greater cold tolerance, the inventor has sought to develop varieties with novel and attractive flower colors and forms, and increased resistance to disease. During the ensuing forty year period, many thousands of unreleased hybrids have been developed by controlled crossing of parents drawn from named (commercially available) cultivars and also drawn from the inventor's own pool of unreleased varieties. Seedlings from these crosses were grown on into mature plants within the inventor's test garden in Chapel Hill, N.C. Included in these grow-out trials were seedlings resulting from a cross made in 1964, as described below, including a single seedling known to the inventor as *Camellia* 60-0-6. *Camellia* 60-0-6 was grown to a mature size, along with other selections from the breeding program, until it was eventually selected by the inventor after the winter of 1985, and later named 'Classic Pink'.

The winter of 1985 was exceptionally severe for the Chapel Hill, N.C. vicinity. Minimum temperatures of −9 degrees Fahrenheit were recorded, at which temperatures *Camellias* are generally killed outright, rather than merely defoliated. Many large plants from the inventor's breeding program were killed outright under these conditions. A small number of varieties survived, including 'Classic Pink' which suffered no damage to its wood and only minor injury to the foliage. The inventor determined that 'Classic Pink' is inherently exceptionally cold hardy for *Camellias.*

'Classic Pink' arose as a single plant from a group of seedlings resulting from the deliberate crossing made by the inventor in 1964 between *Camellia japonica* 'Kumasaka' (unpatented) as male parent, and *Camellia japonica* 'Berenice Boddy' (U.S. Plant Pat. No. 605) as female parent.

'Classic Pink' differs from the parents as follows:

*Camellia japonica* 'Kumasaka' is a peony form of *Camellia* with rose-red flowers and good cold-hardiness, to USDA Hardiness Zone 6b. It is mid- to late-season blooming and has a compact growth habit.

*Camellia japonica* 'Berenice Boddy' is semi-double light pink flowered form of *Camellia* which is early- to mid-season blooming. It is not hardy in regions colder than USDA Hardiness Zone 7.

'Classic Pink' is at least as hardy as *Camellia japonica* 'Kumasaka' but later blooming. In addition, the flowers of 'Classic Pink' are very light pink: lighter pink and more formally double than *Camellia japonica* 'Berenice Boddy'.

The distinguishing traits of 'Classic Pink' are its exceptional cold hardiness combined with attractive plant form comprising compact growth and dark green leaves. The pale pink flowers are novel within the set of cold hardy (to USDA Zone 6) *Camellias* known to the inventor. The lateness of the bloom period for 'Classic Pink' allows 'CLASSIC PINK' to better avoid damage from late spring frosts.

The first asexual reproduction of 'Classic Pink' was conducted by the inventor in 1989 at the inventor's nursery and test garden in Chapel Hill, N.C. The method used for asexual propagation was rooting of semi-hard internodal stem cuttings. The inventor has since determined that 'Classic Pink' reduces true to type in successive generations of asexual reproduction.

SUMMARY OF THE INVENTION

The following traits have been repeatedly observed and represent the characteristics of the new *Camellia* cultivar 'Classic Pink'. These traits in combination distinguish 'Classic Pink' from all other varieties known to the inventor. 'Classic Pink' has not been tested under all possible conditions and phenotypic differences may be observed with variations in environmental, climatic and cultural conditions, without however, any difference in genotype.

1. 'Classic Pink' is one of the most cold-hardy *Camellias* known to the inventor. It has withstood temperatures of −9 degrees Fahrenheit without injury, a temperature at which most *Camellia* cultivars are killed outright.
2. 'Classic Pink' has an attractive compact plant form.
3. The foliage of 'Classic Pink' is very dark glossy green.
4. The flowers of 'Classic Pink' are very pale pink and formal double in form, which combination is considered by the inventor to be new to cold hardy *Camellias*.
5. 'Classic Pink' is sufficiently late to bloom that it mostly avoids injury from late spring frosts.

BRIEF DESCRIPTION OF THE DRAWINGS

The accompanying two color drawings illustrate the overall appearance of the new cultivar 'Classic Pink' showing the colors as true as it is reasonably possible to obtain in colored reproductions of this type. Colors in the photographs may differ from the color values cited in the detailed botanical description, which accurately describe the actual colors of the new variety of *Camellia* named 'Classic Pink'.

The drawing labeled as FIG. 1 (on sheet 1) illustrates a 30 months old (from a cutting) plant of 'CLASSIC PINK' growing in a one gallon container.

Figure 1:
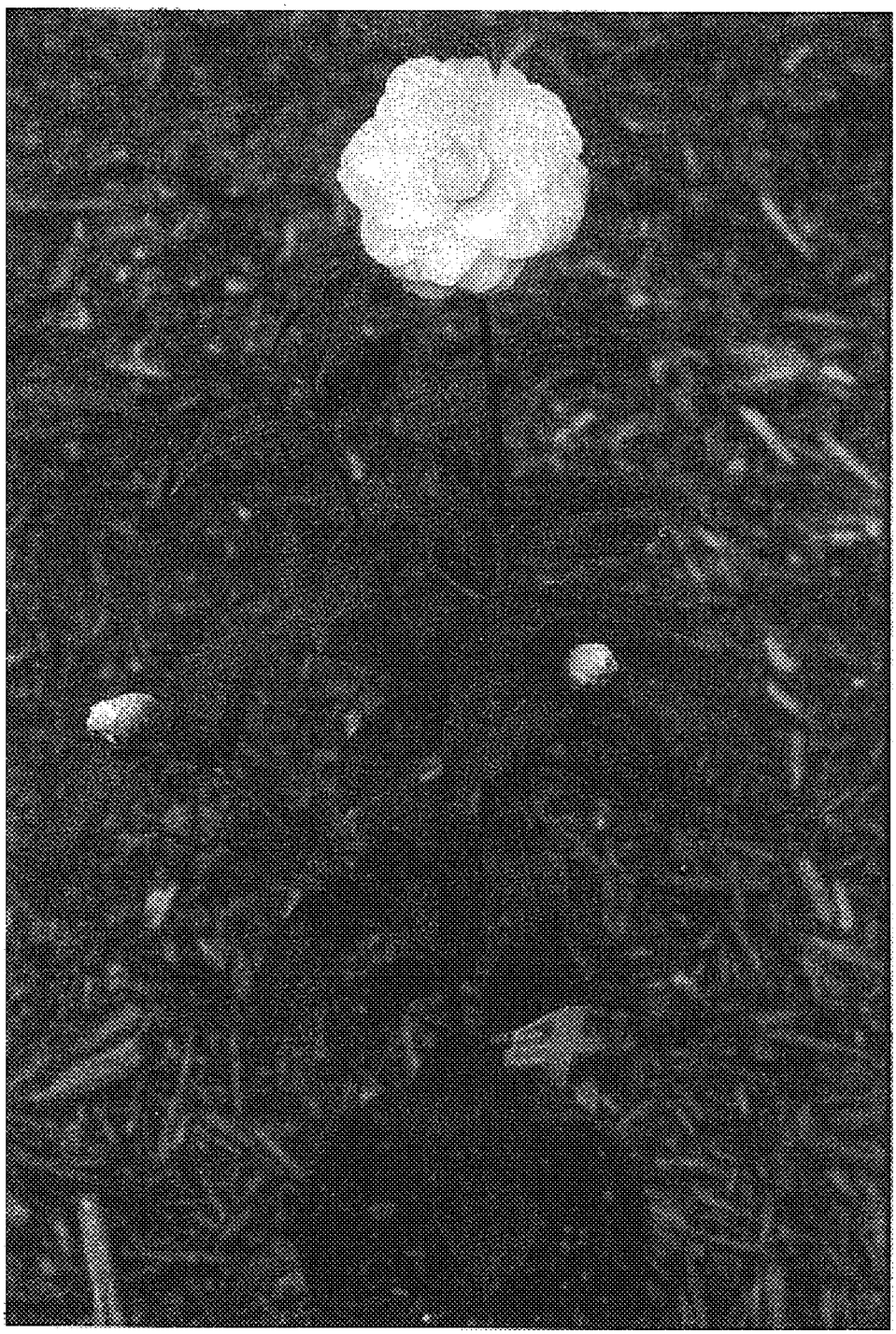
Figure 2:
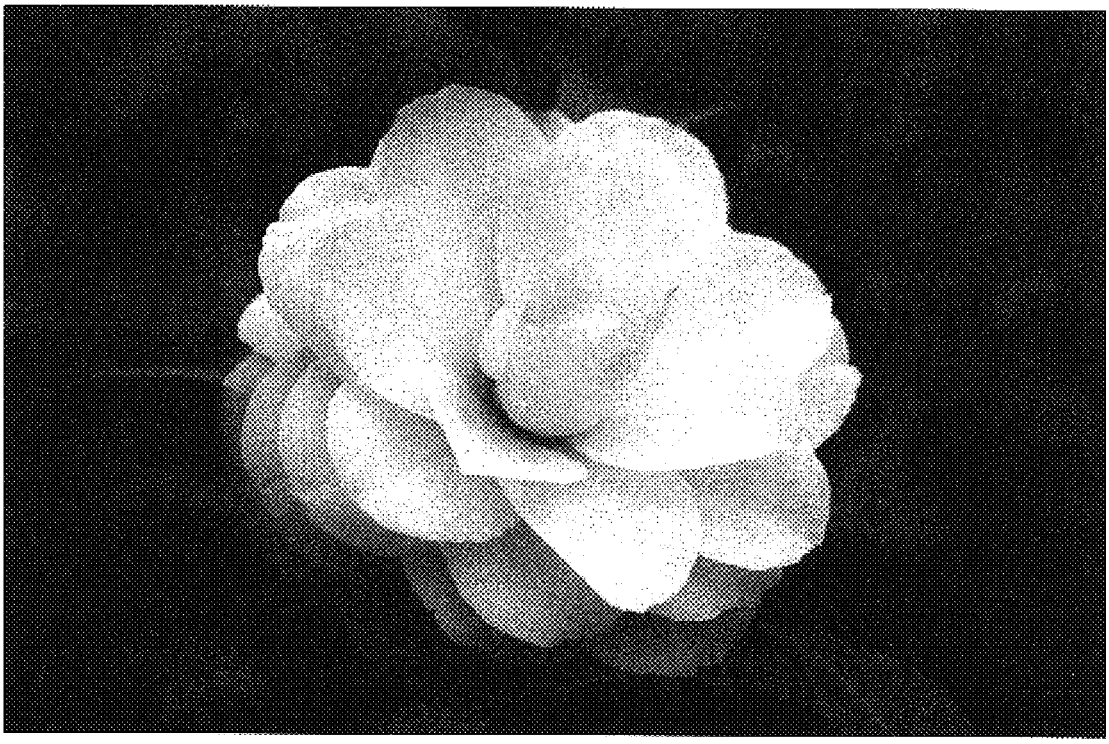

The drawing labeled as FIG. 2 (on sheet 2) illustrates a close-up view of a single flower of 'Classic Pink'.

All drawings were made using conventional techniques and although colors may appear different from actual colors due to light reflectance they are as accurate as possible by conventional photography.

BOTANICAL DESCRIPTION OF THE PLANT

The following is a detailed description of 'Classic Pink' as grown in an open-sided unheated polythene tunnel structure in Chapel Hill, N.C. Data was collected in March and April from plants approximately four years old and growing in a 3 gallon container. The color determinations are in accordance with the 1995 Royal Horticultural Society Colour Chart of The Royal Horticultural Society, London, England, except where general color terms of ordinary dictionary significance are used. The growing requirements are similar to the species.

Family: Theaceae.
Botanical classification: *Camellia japonica.*
Genus: *Camellia.*
Species: *Japonica.*
Variety denomination: 'Classic Pink'.
Common name: Japanese *Camellia.*
Use: Evergreen flowering plant for the landscape.
Container size: Suggested container sizes for planting: 1 gallon, 3 gallon, and above.
Cultural requirements: Plant in woodland setting, sun to partial shade with regular water and well-drained acidic to neutral soil.
Parentage: *Camellia japonica* 'Kumasaka' (Male parent). *Camellia japonica* 'Berenice Boddy' (Female parent).
Plant description:

*Bloom period.*—Flowers start to open in mid-March and continue blooming until early May. Peak bloom is in April.
*Plant habit.*—Compact, dense, upright.
*Vigor.*—Less vigorous (slower growing) than most *Camellias.*
*Dimensions.*—Mature height: approximately 3 meters. Mature width (spread): approximately 2 meters.
*Hardiness.*—USDA Zone 6B.
*Root system.*—Mostly fibrous; can make woody taproot.
*Propagation.*—Propagation is accomplished semi-hardwood stem cuttings.
*Time to develop roots.*—3–4 months.
*Air temperature for rooting.*—15–25° Centigrade.
*Crop time.*—A well-rooted liner can be produced in the first year, and a blooming plant in a 1 gallon pot in two years, with flowering on the previous season's growth. Three to four years can be required to produce a well-branched, well-budded, plant in a three gallon container.
*Disease and pest susceptibility.*—'Classic Pink' is neither less nor more susceptible than the species and other cultivars generally to *Camellia* flower blight, tea scale, oyster scale and *Camellia* scale.

Trunk:

*Trunk shape.*—Cylindrical.
*Main trunk dimensions.*—Up to 15 cm in diameter and 3 meters in height at maturity.
*Trunk surface.*—Slightly rough.
*Trunk color.*—Greyed-white 156C.
*Lenticels.*—Absent.

Branches:

*Branching.*—Typically one trunk with side branches starting low and alternately spaced towards the top where multiple leaders develop.
*Branch shape.*—Cylindrical.
*Branch surface.*—Slightly rough.
*Branch angle at emergence.*—45 degrees.
*Dimensions of branch of a mature plant.*—1 meter in length and 1–2 cm. in diameter.
*Branch color.*—Colors 174B and 165A are both individually present on individual mature branches.
*Internode length.*—2.0–2.5 cm. between nodes.

Foliage:

*Type.*—Evergreen.
*Arrangement.*—Alternate.
*Leaf shape.*—Lanceolate.
*Leaf margins.*—Finely serrate.
*Division.*—Simple.
*Apex.*—Acuminate.
*Base.*—Cuneate.
*Leaf surfaces* (*adaxial and abaxial*).—Glabrous.
*Leaf dimensions.*—9–11 cm. in length and 4–5 cm. in width.
*Leaf color* (*adaxial surface*).—139A.
*Leaf color* (*abaxial surface*).—137C.
*Venation pattern.*—Pinnate.
*Vein color* (*adaxial surface*).—137C.
*Vein color* (*abaxial surface*).—139A.
*Attachment.*—Petiolate.
*Petiole color.*—141C.
*Petiole shape.*—Round.
*Petiole surface.*—Smooth.
*Petiole dimensions.*—11 mm in length and 2 mm. in width.
*Fragrance.*—None.

Flowers:

*Inflorescence type.*—Solitary, formal double (absence of anthers or stigmas).

*Attachment.*—Sessile.

*Arrangement.*—Flowers occur at end of branches or at 1, 2 or 3 nodes from the branch tip.

*Flowers per branch.*—On average, approximately 16 flowers per branch; within the range 10 per branch to 25 per branch.

*Flower shape.*—Circular, radially symmetrical.

*Flower aspect.*—Generally facing upwards; occasionally facing to the side or downwards.

*Flower persistent or self-cleaning.*—Self-cleaning.

*Flower diameter.*—Ranges from 80 mm to 105 mm.

*Flower depth.*—Ranges from 32 mm to 52 mm.

*Flower color.*—Petals (both surfaces) 69D, except white 155B at base.

*Petal number.*—Ranges from 60–100 petals in each flower.

*Petal surface.*—Smooth, slightly cupped.

*Petal length* (*newly opened and flattened*).—25 mm.

*Petal length* (*oldest petals*).—45 mm.

*Petal width* (*newly opened and flattened*).—18 mm.

*Petal width* (*oldest petals*).—25 mm.

*Petal shape.*—Obovate.

*Petal apex.*—Cuspidate.

*Petal base.*—Cuneate.

*Fused or unfused.*—Unfused.

*Petal margin.*—Smooth.

*Bud.*—Shape: Cuspidate. Color (sepals): Sepals towards base: Between 141C and 141D. Sepals near apex: Between 142B and 142C. Dimensions (just prior to opening): 3.6 cm in length and 2.5 cm. in width.

*Calyx.*—Dimensions: 2.1 cm in depth and 3.2 cm in diameter. Surface: Finely pubescent. Color: 141C.

*Sepals.*—Eleven in number. Shape: Reniform. Color (both surfaces): 141C. Dimensions (fully developed flower): Length: 15 mm; Width: 18 mm. Apex: Emarginate. Margins: Fine hairs, feathered edge, sometimes brown and dry.

*Fragrance.*—None.

Reproductive organs:

*Stamens.*—Occasional barely visible malformed stamens, too small to describe.

*Anthers.*—Occasional tiny, three in number possibly, aborted anthers at the floral center.

*Ovary.*—None observed.

*Seed.*—None observed.

What is claimed:

1. A new and distinct cultivar of *Camellia* plant named 'Classic Pink' as described and illustrated herein.

* * * * *